United States Patent [19]

Bilweis

[11] Patent Number: 5,196,022
[45] Date of Patent: Mar. 23, 1993

[54] LIGATURE SYSTEM FOR USE IN ENDOSCOPIC SURGERY, LIGATURE AND HANDLING INSTRUMENT FOR SAID SYSTEM

[75] Inventor: Joseph Bilweis, Noisy le Roi, France
[73] Assignee: Ethicon, Inc., Somerville, N.J.
[21] Appl. No.: 548,943
[22] Filed: Jul. 26, 1990

[30] Foreign Application Priority Data

Dec. 12, 1988 [FR] France .................. 88 16311

[51] Int. Cl.⁵ ........................................ A61B 17/00
[52] U.S. Cl. .................... 606/144; 606/148; 606/139; 606/170
[58] Field of Search ............. 606/144, 148, 151, 139, 606/232, 140, 157, 224, 228

[56] References Cited

U.S. PATENT DOCUMENTS

| 877,476 | 1/1908 | Bach | 606/224 |
|---|---|---|---|
| 3,123,077 | 3/1964 | Alcamo | 606/228 |
| 3,799,169 | 3/1974 | Beroff et al. | 606/224 |
| 4,735,194 | 4/1988 | Stiegmann | 128/6 |
| 4,896,678 | 1/1990 | Ogawa | 606/170 |
| 5,100,418 | 3/1992 | Yoon | 606/144 |

FOREIGN PATENT DOCUMENTS

| 0117981 | 9/1984 | European Pat. Off. | |
| 3504202 | 8/1985 | Fed. Rep. of Germany . | |
| 2600880 | 1/1988 | France . | |
| 1506362 | 4/1978 | United Kingdom . | |
| 8806022 | 8/1988 | World Int. Prop. O. | 606/206 |

Primary Examiner—Stephen C. Pellegrino
Assistant Examiner—Jeffrey A. Schmidt
Attorney, Agent, or Firm—Paul A. Coletti

[57] ABSTRACT

The ligating assembly comprises a trocar (20) and a one-piece element (10) constituted by a body (11) fittable to the end of the trocar, and by a thread (14) extending from said body and forming binding means, the body including a threading channel (16) receiving the free end (15) of the thread at one of its ends and opening out inside the trocar at its other end, the thread and the channel being provided with tightening means such as co-operating notched regions (17, 18) formed on the outside surface of the thread and on the inside surface of the threading channel, serving to hold the thread in place once it has been inserted at least partially into the channel. The assembly may also include means insertable in the trocar for grasping and pulling the free end of the thread after it has been threaded through the threading channel to project beyond the channel inside the trocar, thereby enabling the ligature to be tightened by pulling on the free end. The assembly may also include means, likewise insertable in the trocar, for cutting off the free end of the thread after it has been pulled tight.

6 Claims, 2 Drawing Sheets

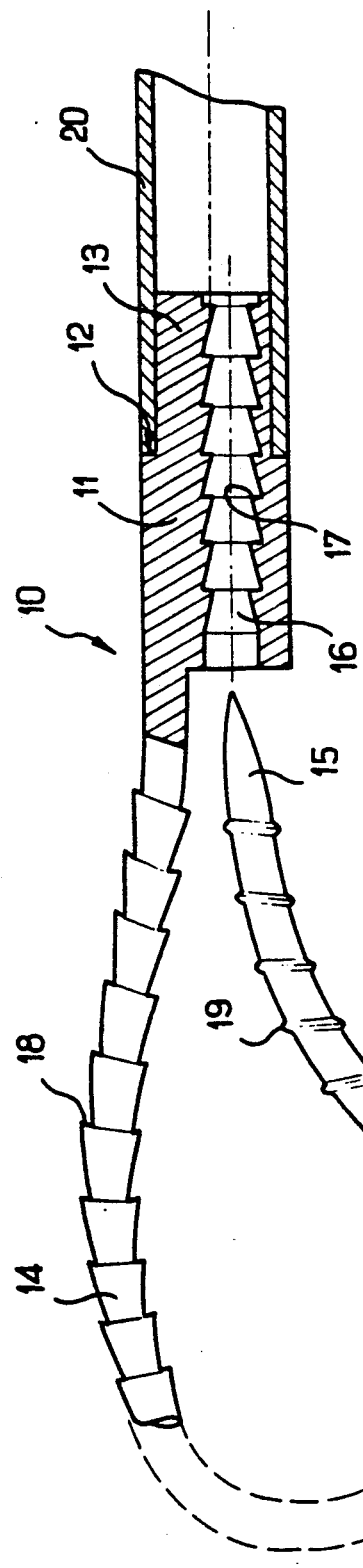
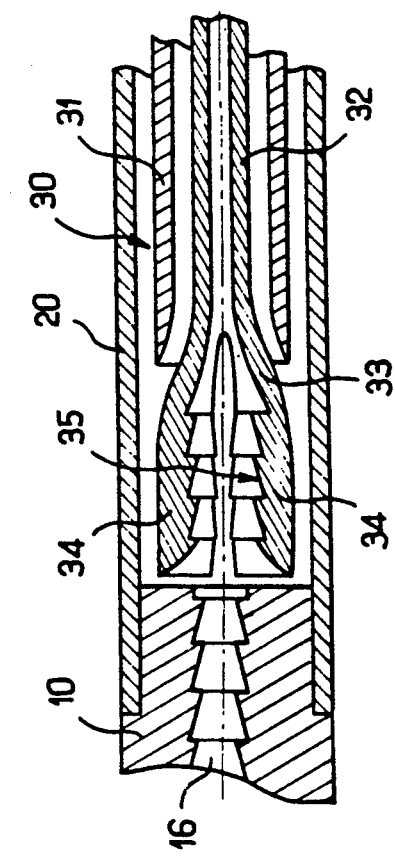
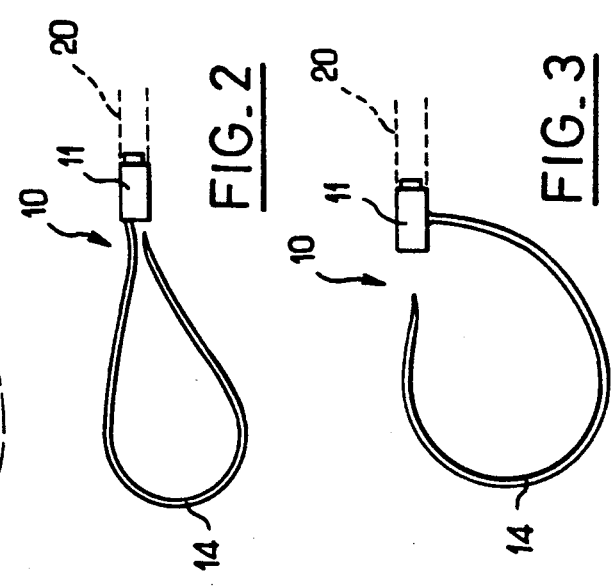

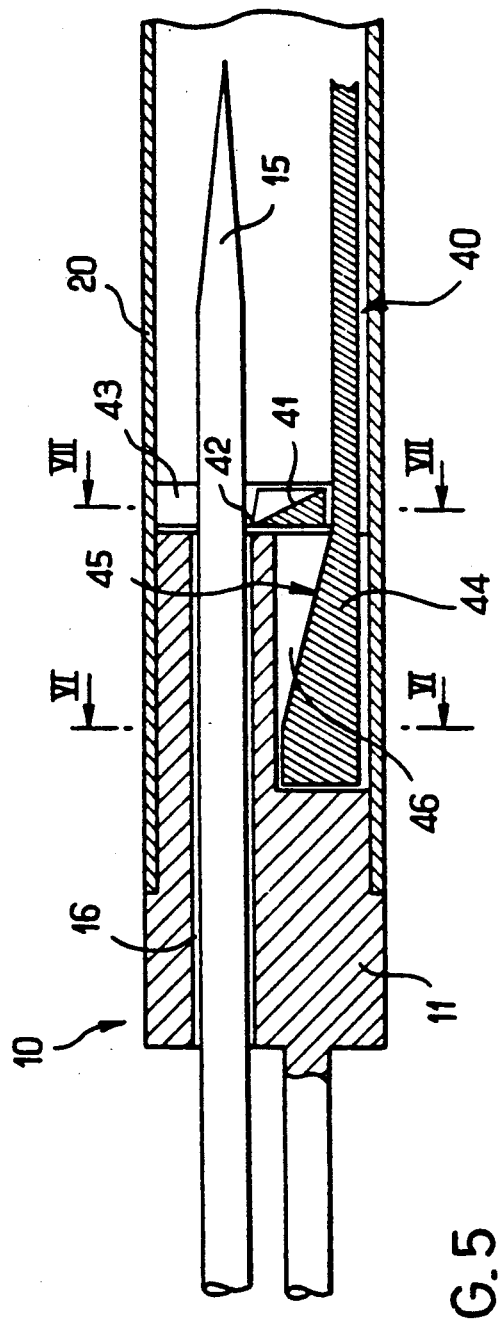
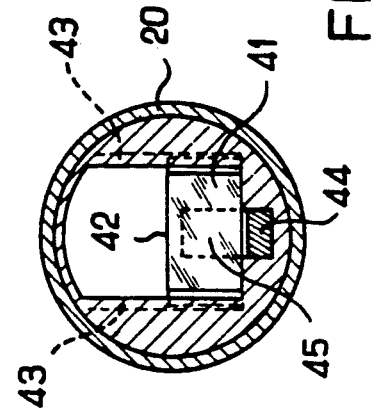
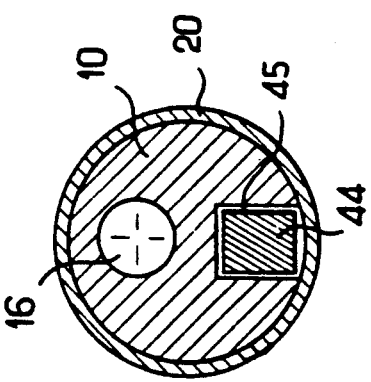

LIGATURE SYSTEM FOR USE IN ENDOSCOPIC SURGERY, LIGATURE AND HANDLING INSTRUMENT FOR SAID SYSTEM

BACKGROUND

This application is a continuation of international application Ser. No. PCT/FR89/00641, filed Dec. 11, 1989, which is designated the United States, now abandoned, such application basing its priority under 35 U.S.C. §119 on French patent application, Ser. No. 88/16311, filed Dec. 12, 1988.

The present invention relates to a ligating assembly for endoscopic surgery.

Endoscopic surgery is a technique which is typically used for intra-abdominal surgery, where the surgeon operates without making an incision in the abdominal wall by passing instruments inside trocar tubes that pass through said abdominal wall. Manipulations are observed via an endoscope inserted in one of the trocar tubes, with the abdominal cavity being previously distended by insufflation of a gas such as $CO_2$ in order to allow manipulation inside the abdominal cavity to be observed.

It is thus possible to install ligatures intra-abdominally. This manipulation consists in passing a binding means around an organ or some tissue and then in knotting and tightening the binding means. Ligatures can thus be installed for closing internal wounds, or around adhesions before or after resection, etc.

In the state of the art, these ligatures are installed in several different ways.

The most elementary technique consists in performing tieing entirely within the body by manipulating the thread while actually inside the abdominal cavity.

In a second technique, a loop is prepared in advance with a slip knot, the loop is then threaded inside the trocar tubes, then the loop is placed around the portion to be ligated, and is tightened by pulling on the slip knot, after which the remaining end of the thread is cut off.

Naturally, this technique can only be applied when it is possible to pass the loop over the part to be ligated, i.e. when said part is constituted by a projecting portion of an organ or of tissue (typical of an adhesion for resection, where it is desired to ligature the remaining portion in order to prevent any infusion or alcohol.

The third technique, referred to as "ligature with extracorporal tieing", consists in inserting a thread in trocar tubes, passing the free end of the thread around the part to be ligated, reinserting said free end in the trocar tube in order to bring it back out from the abdominal cavity at the other end of the trocar tube, tieing a slip knot with said free end around the portion of the thread penetrating into the trocar tube, inserting the resulting loop into the trocar tube so as to cause it to leave via the other end inside the abdominal cavity in the vicinity of the part to be ligated, tightening the knot finally, and then cutting off the remaining end of the thread.

This technique is naturally lengthly and difficult to perform, but it is the only technique which is well adapted to ligating parts over which it is not possible to pass a preconstituted slip knot, typically ligatures which are put into place prior to resection at the root of an adhesion in order to prevent any subsequent hemorrhage at that point, or ligatures for vessels or ducts.

Preferred embodiments of the invention provide a ligating assembly which is quick and easy to use, and which can be used regardless of the shape of the part to be ligated, thereby avoiding the difficulties relating to the extra-corporal tieing technique.

To this end, the present invention provides a ligating assembly comprising a trocar, and a one-piece element constituted by a body fittable in the end of said trocar tube, and by a thread extending from said body and constituting binding means, the body including a threading channel receiving the free end of the thread at one of its end and opening out to the inside of the trocar tube at its other end, the thread and the channel being provided with tightening means for retaining the thread in position once it has been inserted at least partially into the channel.

Thus, essentially, the tieing operation (prior tieing of a slip knot, or extra-corporal tieing) is replaced by a threading and tightening operation which is always easier to perform.

Preferably, the tightening means comprise co-operating notched regions formed on the outside surface of the thread and on the inside surface of the threading channel.

In an advantageous embodiment, the ligating assembly also comprises grasping and pulling means insertable inside the trocar tube for grasping and pulling the free end of the thread once threaded through the threading channel and projecting therefrom into the trocar tube, thereby enabling the ligature to be tightened by pulling on said free end.

As a result, once the free end of the thread has been inserted far enough into the threading channel, the surgeon can tighten the binding without any need to continue pushing said free end into the threading channel. It suffices to actuate a simple movement of the grasping and pulling means in order to tighten the ligature fully.

Advantageously, these grasping and pulling means comprise, for example, two telescopic elements axially moveable relative to each other, one of the elements being provided with jaws for grasping and clamping onto the free end of the thread, the two elements being such that relative axial movement thereof causes the jaws to move towards each other and clamp onto the free end of the thread, with simultaneous axial movement of the two elements then pulling said free end and consequently tightening the ligature.

The ligating assembly may also include cutting-off means insertable into the trocar tube for cutting off the free end of the thread after it has been pulled; these cutting-off means advantageously comprise, for example, a guillotine which is moveable inside the trocar tube, transverse guide means for guiding the guillotine, and actuator means for driving the guillotine in transverse motion after the free end of the thread has been fully tightened.

Thus, in addition to installing and tightening the ligature, the free end thereof projecting outside the body of the one-piece element is cut-off quickly and completely safely. The cutting operation takes place inside the trocar tubes, thereby avoiding the need to use a separate cutting instrument inserted via another trocar tube, as has always been required in the past, and thus requiring observation via an endoscope in order to be put into place and actuated.

An embodiment of the invention is described by way of example and with reference to the accompanying drawings, in which:

FIG. 1 is a view of a ligating assembly of the invention, shown partially in section;

FIGS. 2 and 3 show two possible variant forms of ligature;

FIG. 4 shows the means for grasping and pulling the free end of the thread;

FIG. 5 shows means for cutting off the free end of the thread; and

FIGS. 6 and 7 are sections respectively on lines VI—VI and VII—VII of the means shown in FIG. 5.

FIG. 1 shows a ligature 10 installed at the end of a trocar tube 20 inserted into the body of a patient, e.g. inside the abdominal cavity.

The ligature 10 comprises a body 11 provided with a shoulder 12 coming into abutment against the end of the trocar tubes 20 so that a portion 13 of the body is a push-fit inside the trocar. In this way, and unlike present tieing systems (slip knot or extra-corporal tieing), the surgeon has no need for a separate instrument to bring the ligature into the vicinity of the part to be ligated since it suffices to guide the trocar 20 carrying the ligature 10 fixed at its end.

At its end opposite from that inserted in the trocar, the ligature 10 has a flexible thread 14 extending from said body and constituting the binding means per se.

As can be seen in FIGS. 2 and 3, the thread may extend from the body 11 in a direction which is substantially parallel to the axis of the trocar tubes 20 (as shown in FIG. 2) or else in a direction perpendicular to said axis (as shown in FIG. 3). Which particular ligature configuration is selected will depend essentially on the shape and size of the part to be ligated.

The free end 15 of the thread 14 is designed to be inserted into a threading channel 16 running right through the body 11 along a substantially axial direction. When inserted in the channel 16, the free end 15 is capable of extending out through the other end into the trocar tubes 20.

The loop is tightened by continuing this movement whereby the thread is inserted into the channel 16. In order to prevent the ligature coming loose after it has been tightened, the thread 14 has a first notched region 18, and the inside of the threading channel 16 has a second notched region 17, which regions co-operate so as to prevent the thread moving back out from the threading channel (with the dimensions and the shapes of the notched portions 17 and 18 being appropriately designed to ensure this non-return effect).

The portion of the thread closes to its free end 15 is preferably not provided with notches 18, but is merely provided with smaller projecting collars 19 which serve to hold the thread inside the channel 16 and prevent it from slipping (the collars 19 co-operating with the notches 19), while not preventing the thread from being pulled out if traction is exerted thereon. Thus, after passing the thread around the part to be ligated, the surgeon may insert it partially into the threading channel while still having the option, if necessary, of enlarging the loop, for example in order to enable it to be displaced. Once the loop has been put exactly into position, it can then be tightened fully and irreversibly.

The ligature 10 is made of a biologically inert material (generally a plastic material) or even, where appropriate, of a bioadsorbable material.

In the simplest implementation of this ligature, the free end 15 may be grasped by an instrument manipulated by the surgeon, passing through the channel 16 and then actuated until the loop is fully tightened.

However, this operation may be simplified by providing specific tightening means.

FIG. 4 shows such means 30 in the form of an instrument constituted by two portions 31 and 32 telescopically received one inside the other and both inserted inside the trocar tube 20. The element 31 is a right cylindrical tube, and the element 32 is a tube of smaller diameter lying inside the other tube 31, and having a flared portion 32 where it projects beyond the tube 31. The end of the inner tube 32 is shaped to form jaws each provided with internal notches 35 of substantially the same shape as the notches 18 on the thread 14. These jaws are placed over the channel 16 so as to be able to grasp the free end 15 after it has been threaded through said channel to project between the jaws 34. Then, by sliding the two tubes 31 and 32 relative to each other, the end of the tube 31 is brought to bear against the flared portion 33 of the tube 32, thereby closing the jaws 34 on the free end of the thread.

With the free end clamped in this way between the jaws, it can be withdrawn by pulling both tubes 31 and 32 simultaneously until the ligature is fully tightened. The jaws can then be reopened and the ligature 10 released from the trocar tube 20.

The surgeon can then cut off the portion of the thread projecting away from the loop beyond the end of the threading channel.

This operation may be performed manually in conventional manner using a cutting instrument manipulated under endoscopic observation.

However, this operation may be simplified by using specific cutting-off means situated inside the trocar tube 20.

FIG. 5 (together with the sections of FIGS. 6 and 7) illustrates such cutting-off means.

These means 40 are essentially constituted by a guillotine 41, i.e. an element mounted to slide transversely relative to the axis of the trocar tube, said guillotine being provided with a cutting edge 42 that performs the cutting-off operation per se, and being guided in its transverse displacement by grooves 43.

The guillotine 41 is operated by a slider 44 provided with a sloping portion 45 that is initially received in a cavity 46 formed in the body 11 of the one-piece element.

Once a sufficient length of the free end 15 has been passed through the threading channel 16 to enable the loop to be tightened down to the required size, with the free end being locked in place by the co-operating notched regions (not shown in FIG. 5), then the free end can be cut off by pulling the slider 41 rearwards, thereby camming the guillotine 41 transversely and thus cutting off the free end 15 level with the outlet from the channel 16.

It may be observed that the cut-off portion remains inside the trocar and that there is therefore no risk of it being lost and requiring recovery by additional manipulation.

Although the cutting-off means of FIG. 5 are shown in isolation, they may naturally be combined with the grasping and pulling means of FIG. 4 into a single instrument serving to perform all of the operations required for putting a ligature into place.

I claim:

1. A ligating assembly for endoscopic surgery, comprising:

a trocar tube; and a one-piece element constituted by a body fittable in mating relationship with the end of said trocar tube, and by a thread having a free end extending from said body and constituting binding means, the body including a threading channel receiving the free end of the thread at one of its ends and opening out to the inside of the trocar tube at its other end, the thread and the channel being provided with tightening means for retaining the thread in position once it has been inserted at least partially into the channel; and further comprising cutting means insertable into the trocar tube for cutting off the free end of the thread, said cutting means including a guillotine movable inside the trocar tube, and transverse guide means for guiding said guillotine.

2. A ligating assembly according to claim 1, in which the tightening means comprise co-operating notched regions formed on the outside surface of the thread and on the inside surface of the threading channel.

3. A ligating assembly according to claim 2, and further comprising:

grasping and pulling means insertable inside the trocar tube for grasping and pulling the free end of the thread once threaded through the threading channel and projecting therefrom into the trocar tube, thereby enabling the ligature to be tightened by pulling on said free end.

4. A ligating assembly according to claim 3, in which the means for grasping and pulling the free end of the thread comprise two telescopic elements axially moveable relative to each other, a first of said telescopic elements being provided with jaws for grasping and clamping onto the free end of the thread, the second of said telescopic elements being such that relative axial movement thereof causes the jaws to move towards each other and clamp onto the free end of the thread, with simultaneous axial movement of the two said telescopic elements then pulling said free end and consequently tightening the ligature.

5. A ligating assembly according to claim 1, in which the cutting-off means include actuator means for driving the guillotine in transverse motion after the free end of the thread has been fully tightened.

6. The ligating assembly according to claim 1, further comprising grasping and pulling means insertable in the trocar for grasping and pulling the free end of the thread once threaded through the threading channel and projecting therefrom into the trocar tube, thereby enabling the ligature assembly to be tightened by pulling on said free end.

* * * * *